United States Patent
Racowsky et al.

(10) Patent No.: US 11,579,084 B2
(45) Date of Patent: Feb. 14, 2023

(54) DEVICES, SYSTEMS, AND METHODS FOR FLUORESCENCE LIFETIME IMAGING MICROSCOPY

(71) Applicants: President and Fellows of Harvard College, Cambridge, MA (US); The Brigham and Women's Hospital, Inc., Boston, MA (US)

(72) Inventors: Catherine Racowsky, West Roxbury, MA (US); Manqi Deng, Natick, MA (US); Daniel Needleman, Somerville, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/218,283

(22) Filed: Mar. 31, 2021

(65) Prior Publication Data

US 2021/0239615 A1 Aug. 5, 2021

Related U.S. Application Data

(60) Division of application No. 15/620,945, filed on Jun. 13, 2017, now abandoned, which is a continuation of
(Continued)

(51) Int. Cl.
*G01N 21/64* (2006.01)
*A61B 17/425* (2006.01)

(52) U.S. Cl.
CPC ....... *G01N 21/6408* (2013.01); *A61B 17/425* (2013.01); *G01N 21/6428* (2013.01);
(Continued)

(58) Field of Classification Search
CPC .......... G01N 21/6408; G01N 21/6428; G01N 2021/6423; G01N 2201/12761;
(Continued)

(56) References Cited

U.S. PATENT DOCUMENTS

| | | | |
|---|---|---|---|
| 5,541,081 A * | 7/1996 | Hardy ................ | G01N 33/5091 435/25 |
| 7,049,480 B1 | 5/2006 | Christmann et al. | |

(Continued)

FOREIGN PATENT DOCUMENTS

| | | |
|---|---|---|
| JP | 2010004789 A | 1/2010 |
| WO | 1995025810 A1 | 9/1995 |

(Continued)

OTHER PUBLICATIONS

Skala et al. In vivo multiphoton microscopy of NADH and FAD redox states, fluorescence lifetimes, and cellular morphology in precancerous epithelia, Proceedings of the National Academy of Sciences vol. 104 No. 49, pp. 19494-19499 (Year: 2007).*

(Continued)

*Primary Examiner* — David P Porta
*Assistant Examiner* — Jeremy S Valentiner
(74) *Attorney, Agent, or Firm* — Nixon Peabody LLP; David S. Resnick; Nicole D. Kling

(57) ABSTRACT

The invention provides novel non-invasive in vitro methods for assessing the metabolic condition of oocytes and/or embryos with fluorescence lifetime imaging microscope, that can be used, for example, in assessment of oocytes and embryos in assisted reproductive technologies.

17 Claims, 1 Drawing Sheet

Related U.S. Application Data application No. 14/759,591, filed as application No. PCT/US2014/010435 on Jan. 7, 2014, now abandoned.

(60) Provisional application No. 61/750,061, filed on Jan. 8, 2013.

(52) U.S. Cl.
CPC ..... *G01N 21/6458* (2013.01); *G01N 21/6486* (2013.01); *G01N 2021/6423* (2013.01); *G01N 2201/06193* (2013.01); *G01N 2201/12761* (2013.01)

(58) Field of Classification Search
CPC ........... G01N 21/6458; G01N 21/6486; G01N 2201/06193; A61B 17/425
See application file for complete search history.

(56) References Cited

U.S. PATENT DOCUMENTS

| | | |
|---|---|---|
| 7,698,000 B2 | 4/2010 | Silberberg et al. |
| 7,907,769 B2 | 3/2011 | Sammak et al. |
| 8,489,337 B2 | 7/2013 | Hyde et al. |
| 8,497,063 B2 | 7/2013 | Schenk et al. |
| 2008/0240527 A1 | 10/2008 | Keller |
| 2008/0247628 A1 | 10/2008 | Ramsing et al. |
| 2009/0163764 A1 | 6/2009 | Sher et al. |
| 2009/0184259 A1 | 7/2009 | Ma et al. |
| 2010/0195877 A1 | 8/2010 | Oonishi et al. |
| 2011/0319984 A1 | 12/2011 | Hyde et al. |
| 2012/0142069 A1 | 6/2012 | Shea et al. |
| 2012/0276578 A1 | 11/2012 | Stringari et al. |

FOREIGN PATENT DOCUMENTS

| | | |
|---|---|---|
| WO | 2007080443 A3 | 7/2007 |
| WO | 2013006948 A1 | 1/2013 |

OTHER PUBLICATIONS

Berezin et al. Fluorescence lifetime measurements and biological imaging, Chemical Reviews vol. 110, No. 5, pp. 2641-2684 (Year: 2010).*
Heikal Intracellular coenzymes as natural biomarkers for metabolic activities and mitochondrial anomalies, Biomarkers in Medicine vol. 4, No. 2, pp. 241-263 (Year: 2010).*
Gardner et al. Analysis of metabolism to select viable human embryos for transfer, Fertility and Sterility vol. 99, No. 4, pp. 1062-1072 (Year: 2013).*
Buryakina et al., Monitoring cellular metabolism of 3T3 upon wild type E. coli infection by mapping NADH with FLIM, Oct. 10, 2010, Chinese Optics Letters, vol. 8, No. 10, pp. 931-933 (Year: 2010).*
Becker & Hickl GmbH, FLIM Systems for Zeiss LSM-710, May 2010, 4 pages.
Berezin et al., "Fluorescence lifetime measurements and biological imaging." Chemical Reviews 110(5):2641-2684 (2010).
Botros et al., "Metabolomics and its application for non-invasive embryo assessment in IVF", Molecular Human Reproduction 14(12):679-690 (2008).
Buryakina et al., "Monitoring cellular metabolism of 3T3 upon wild type E. coli infection by mapping NADH with FLIM", Chinese Optics Letters 8(10):931-933 (2010).
Carl Zeiss MicroImaging GmbH, LSM 710 Brochure 60-1-0001/e, Jan. 2008, 33 pages.
Carl Zeiss Microscopy GmbH, System Solutions for Live Cell Imaging under Physiological Conditions Brochure 60-2-0001/e, Feb. 2008, 42 pages.
Fernandes et al., "NLRP5 Mediates Mitochondrial Function in Mouse Oocytes and Embryos", Biology of Reproduction 8(5):138, 1-10 (2012).
Gadella et al., "Fluoresence lifetime imaging microscopy (FLIM): Spatial resolution of microstructures on the nanosecond time scale", Biophysical Chemistry 48:221-239 (1993).
Gardner et al. (Eds.) "Human Gametes and Preimplantation Embryos", Chapters 20, 21, and 23, Springer Science and Business Media New York (2013).
Ghukasyan et al. "Characterization of the NADH lifetime at different cell densities in a culture." Proceedings of SPIE 6860(68602B): 1-8 (2008).
Ghukasyan et al., "Monitoring Cellular Metabolism with Fluorescence Lifetime of Reduced Nicotinamide Adenine Dinucleotide", J. Phys. Chem. 113:11532-11540 (2009).
Heikal, "Intracellular coenzymes as natural biomarkers for metabolic activities and mitochondrial anomalies", Biomark Med. 4(2):241-263 (2010).
Hsieh et al., "Higher harmonic generation microscopy of in vitro cultured mammal oocytes and embryos", Optics Express 16(15):11574-11588 (2008).
Huang et al. "Two-Photon Fluorescence Spectroscopy and Microscopy of NAD(P)H and Flavoprotein." Biophysical Journal 82(5): 2811-2825 (2002).
Kyvelidou et al., "Following the course of pre-implantation embryo patterning by non-linear microscopy." Journal of Structural Biology 176(3):379-386 (2011).
Mayevsky et al., "Mitochondrial fucntion in vivo evaluated by NADH fluorescence: from animal models to human studies", Am J Physiol Cell Physiol. 292:C615-C640 (2007).
Niesner et al. "Selective Detection of NADPH Oxidase in Polymorphonuclear Cells by Means of NAD(P)H-Based Fluorescence Lifetime Imaging." Journal of Biophysics 2008(602639): 1-13 (2008).
Quinn et al., "The Relationships Between the ATP Content of Preimplantation Mouse Embryos and Their Development in Vitro During Culture", J Reprod. Fert. 35(2):301-309 (1973).
Ross, Microscopy Optical Sectioning, May 2010, 66 pages.
Skala et al., "In vivo microscopy of NADH and FAD redox states, fluorescence lifetimes, and cellular morphology in precancerous epithelia", PNAS 104(49): 19494-19499 (2007).
Vergouw et al., "Day 3 embryo selection by metabolomic profiling of culture medium with near-infrafred spectroscopy as an adjunct to morphology: a randomized controlled trial", Human Reproduction 27(8):2304-2311 (2012).
Yu et al., "Two-photon autofluorescence dynamics imaging reveals sensitivity of intracellular NADH concentration and conformation to cell physiology at the single-cell level." Journal of Photochemistry and Photobiology B: Biology 95 (1):46-57 (2009).

* cited by examiner

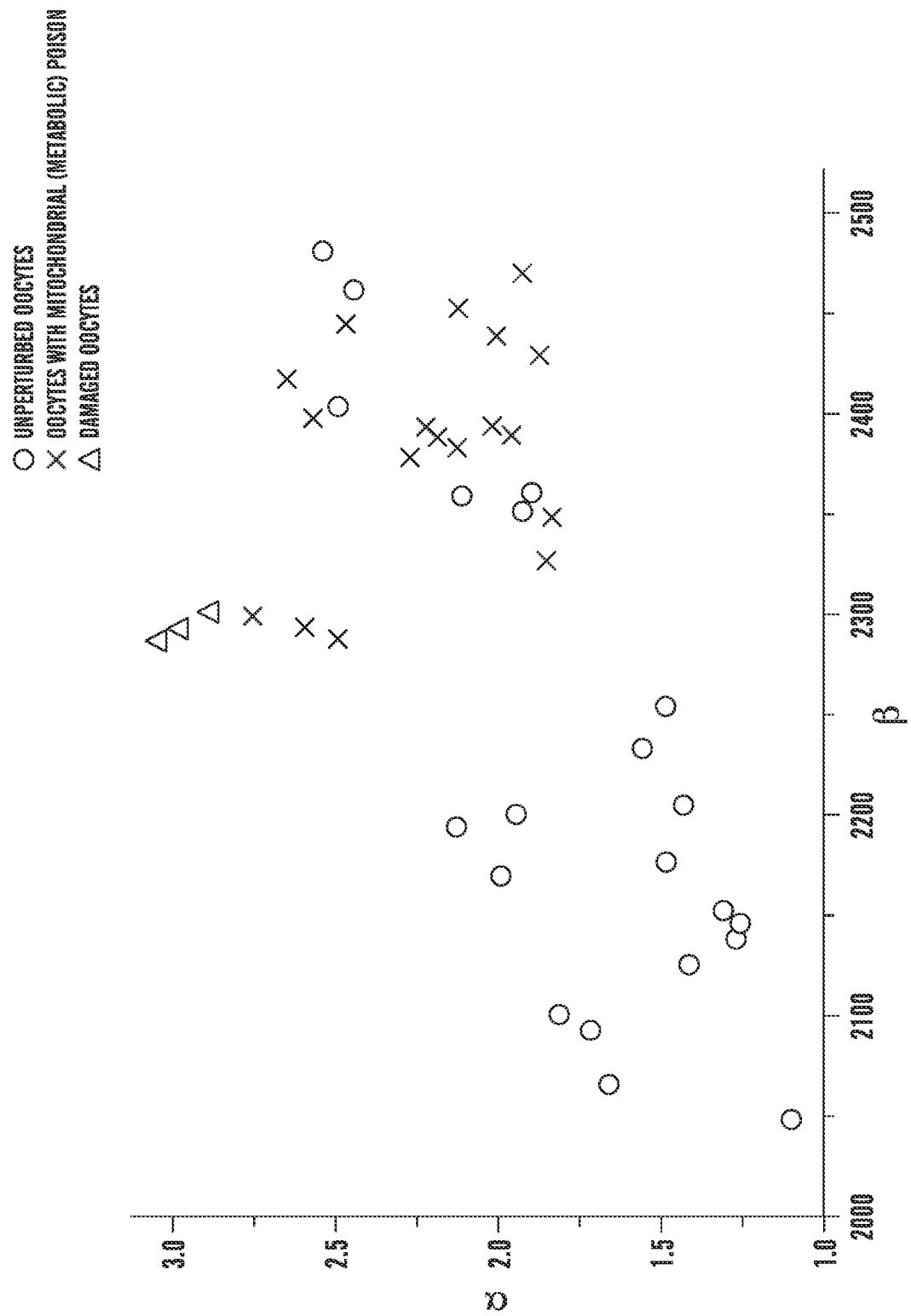

DEVICES, SYSTEMS, AND METHODS FOR FLUORESCENCE LIFETIME IMAGING MICROSCOPY

CROSS-REFERENCE TO RELATED APPLICATION

This application is a divisional under 35 U.S.C. § 121 of co-pending U.S. application Ser. No. 15/620,945 filed Jun. 13, 2017, which is a continuation under 35 U.S.C. § 120 of U.S. application Ser. No. 14/759,591 filed on Jul. 7, 2015 now abandoned, which is a 35 U.S.C. § 371 National Phase Entry Application of International Application No. PCT/US14/10435 filed Jan. 7, 2014, which claims benefit under 35 U.S.C. § 119(e) of U.S. Provisional Application No. 61/750,061 filed Jan. 8, 2013, the contents of which are incorporated herein by reference in their entireties.

FIELD OF THE INVENTION

The invention relates to methods for assessing the metabolic condition of oocytes and/or embryos, and can be used, e.g., in assessment of oocytes and embryos in assisted reproductive technologies.

BACKGROUND

Assisted Reproductive Technology (ART) has revolutionized the treatments of human infertility in the past 30 years and has become ubiquitous. ART currently accounts for over 1% of birth in the U.S. (SART, 2005). However, success rates for ART are low, only 10%-35% of cycles result in successful birth, leading to high costs and use of multiple embryos, which in turn gives rise to high rates of multiple gestations. Multiple gestations greatly increase mortality rates and suffering for both infant and mothers, and produce substantial financial costs. It has been estimated that complications from multiple pregnancy from ART account for approximately one billion dollars of health care cost annually in the U.S. (Bromer and Seli, 2008).

One of the major reasons for the low success rate of ART is the absence of reliable methods for selecting the highest quality embryo(s) for transfer. The lack of methods for assessing embryo quality has led to substantial efforts to develop improved assays of embryo viability. The current most reliable method for predicting embryo quality is to examine embryo morphology prior to transfer using standard transmitted light microscopy systems, with some clinics exploring the utility of time-lapsing imaging using specialized microscopes such as the EmbryoScope by Unisense or EPIC by Auxogyn. However, selection criteria generally remain subjective and only result in the ~35% success rate quoted above. Newly proposed non-microscopy based methods, using genomic, transcriptomic or proteomic based assays (Uyar, et al, 2012), require a biopsy of the embryo and are thus invasive and significantly reduce rates of embryo survival (Scott et al., 2006). A metabolomic approach which initially showed promise was to assay the metabolic state of the embryo by measuring changes in metabolites in the embryo culture media (Botros, et al. 2008). However, a prospective randomized trial has recently failed to show that utilization of such metabolomic assessment improves selection over morphologic evaluation alone (Vergouw et al, 2012).

Minimally invasive, simple and reliable methods for assessing embryo or oocyte viability for assisted reproductive technologies would provide a significant advance for improving the safety of the mother and the fetus, and would also reduce the costs of the assisted reproductive technologies by reducing the number of times one has to try implantation to get pregnant and also by reducing multiple gestations.

SUMMARY OF THE INVENTION

We provide an integrated, automated system for rapidly determining oocyte and embryo quality. The described methods are minimally invasive. We have discovered that a direct analysis of the metabolic state of these cells without additional manipulations of the cells or the cell culture media can be performed reliably and rapidly, and in most cases minimally invasively using fluorescence lifetime imaging microscopy (FLIM) of NADH and/or FAD in an in vitro assay.

Thus, we provide methods for assessing oocytes and embryos either using oocytes or complete embryos or by using granulosa or cumulus cells associated with the oocytes or one or more cells biopsied from the embryo by analyzing their metabolic state using autofluorescence from nicotinamide adenine dinucleotide (NADH) and/or flavin adenine dinucleotide (FAD) with FLIM. Cells with objectively measured adequate metabolic state as indicated by fluorescent lifetime of protein bound and/or free NADH or protein bound and/or free FAD indicate an oocyte or embryo that can be selected for in vitro fertilization or implantation, and if the metabolic state is inadequate the oocyte/embryo can be discarded from in vitro fertilization or implantation.

For example, we showed that unperturbed oocytes exhibit a range of values of alpha and beta (FIG. 1, circles). As seen in FIG. 1, oocyte quality depends on oocyte metabolic state. Oocyte metabolic state can be rapidly, non-invasively, and quantitatively measured by Fluorescence Lifetime Imaging Microscopy (FLIM) of FAD or NADH. Two parameters (alpha and beta) are extracted from FLIM measurements of NADH (or FAD) in oocytes. In the example, we used mouse oocytes but similar calculations are expected to work for human oocytes, as the mammalian cells, such as mouse and human cells are relatively similar, particularly relating to their metabolic state, at this stage. Each point corresponds to data from a single oocyte. Perturbing oocytes by specific metabolic inhibitors (black crosses), or non-specific damage (triangles) causes both parameters to increase. Unperturbed oocytes (circles) exhibit a range of values of alpha and beta. These parameters are indicative of oocyte quality.

One can compare the NADH/FAD autofluorescence lifetime to a reference distribution which provides a convenient way of selecting viable and non-viable oocytes/embryos.

The lifetime distribution of NADH/FAD can be approximated as a sum of two exponentials. The parameter α is the ratio of the amplitude of the two exponentials, the parameter, β, is the lifetime of the longer exponential. Increase in both alpha and beta of NADH was found to be indicative of damage in the embryo/oocyte. Thus, typically, cells with increased alpha and beta values compared to a reference value are discarded from ART methods as they would be considered damaged and alpha and beta less than a reference value would be selected for ART methods as their metabolic activity is indicative of healthy activity.

The FLIM measurements according to the methods of the invention can be performed with extremely low levels of illumination, which is far less than is currently used in in vitro fertilization clinics to determine the morphology of oocytes and embryos. Therefore, the FLIM measurements performed according to the methods of the present invention will not perturb oocytes and embryos and are thus as non-invasive as possible.

Accordingly, we provide a method for assessing the quality of an oocyte or an embryo, the method comprising (a) exposing a test cell selected from the oocyte or an oocyte-associated cumulus cell or the embryo or a cell from the embryo to a fluorescence lifetime imaging microscope (FLIM) to acquire a fluorescence lifetime histogram of auto-fluorescence of endogenous NADH or FAD for the test cell; (b) averaging the fluorescence lifetime histogram of NADH auto-fluorescence or FAD auto-fluorescence or both over the entire test cell, or the cytoplasm of the test cell, or mitochondria of the test cell; (c) comparing the averaged fluorescence lifetime histogram from the test cell to an averaged fluorescence lifetime histogram reference value to determine if the measured averaged fluorescence lifetime histogram from the test cell differs statistically from that of the reference value; and (d) if the averaged fluorescence lifetime histogram from the test cell does not differ statistically from the reference value then selecting the oocyte for in vitro fertilization or embryo for implantation and if the averaged fluorescence lifetime histogram from the test cell differs statistically from the reference value then excluding the oocyte from in vitro fertilization or embryo from implantation.

In some aspects of all the embodiments of the invention, the method comprises a step of establishing the statistical significance by fitting lifetime histograms to a sum of two exponentials and the parameters of the measured cells are deemed to fall within or not fall within the range of parameters found in the healthy cells.

In some aspects of all the embodiments of the invention, the parameters to be compared between the measurements and the healthy cells are alpha, defined as the ratio of the amplitude of the two exponentials, and beta, defined as the lifetime of the longer exponential.

In some aspects of all the embodiments of the invention, the maximum value of alpha from the healthy cells is a specific value within the range 1.0-4.0 and the corresponding maximum value of beta of healthy cells is in the range 2000 ps-3000 ps.

In some aspects of all the embodiments of the invention, the FLIM is performed using a wavelength of about 740 nm in two-photon fluorescence excitation and using an emission bandpass filtered centered around about 460 nm.

In some aspects of all the embodiments of the invention, the FLIM is performed using a wavelength of about 340 nm in one-photon fluorescence excitation and using an emission bandpass filtered centered around about 460 nm.

In some aspects of all the embodiments of the invention, the FLIM is performed in the frequency domain instead of the time domain.

In some aspects of all the embodiments of the invention, the FLIM is performed using a wavelength of about 900 nm in two-photon fluorescence excitation and using an emission bandpass filtered centered around about 550 nm.

In some aspects of all the embodiments of the invention, the FLIM is performed using a wavelength of about 450 nm in one-photon fluorescence excitation and using an emission bandpass filtered centered around about 550 nm.

In all aspects of the invention, the methods are performed in vitro. The noninvasive nature of the methods allows them to be performed without harming the embryos or oocytes.

These and other aspects of the invention, as well as various advantages and utilities, will be more apparent with reference to the detailed description of the preferred embodiments and to the accompanying drawings.

BRIEF DESCRIPTION OF DRAWINGS

FIG. 1 shows data from FLIM imaging of NADH in mouse oocytes. Non-linear microscopy was used to assess the quality of live oocytes and embryos. FLIM curves from individual oocytes were fit to the sum of two exponentials. The parameter $\alpha$, is the ratio of the amplitude of the two exponentials, the parameter, $\beta$, is the lifetime of the longer exponential in picoseconds. Each point corresponds to data from a single oocyte. Unperturbed oocytes exhibit a range of values of $\alpha$ and $\beta$. Perturbing oocytes by specific metabolic inhibitors (black crosses) or non-specific damage (triangles) causes both parameters to increase.

DETAILED DESCRIPTION OF THE INVENTION

We have discovered that the metabolic state of an oocyte or an embryo can be directly assessed using FLIM imaging of the autofluorescence of the cellular metabolites inside the oocyte or the embryo or using one or more cumulus cells that surround the oocyte or a cell biopsied from the embryo. Oocytes and embryos with acceptable metabolic status can then be selected for in vitro fertilization or implantation and oocytes and embryos having abnormal metabolic status can be discarded from further assisted reproductive methods. The methods provide a way to analyze embryos/oocytes with a process that is much less invasive than any method we are aware of.

The methods for assessing embryo quality are useful for predicting which embryos have the greatest potential for implantation in order to: (i) increase pregnancy rates with assisted reproductive technologies; (ii) decrease multiple pregnancy rates by justifying transfer of the single "best" embryo; and (iii) appropriately select suitable embryos for cryopreservation and (iv) increase the efficiency of offspring from transgenic intervention. The methods for assessing embryo quality are also useful for assessing the impact or effect of current invasive procedures on the oocyte and embryo, including: (i) intracytoplasmic sperm injection; and (ii) blastomere biopsy for pre-implantation cytogenetic diagnosis.

In the current methods we apply FLIM to detection of metabolic state of embryos and/or oocytes by direct analysis of the embryos or oocytes or analysis of cells from embryos or analysis of cumulus or granulosa cells surrounding the oocytes.

As used herein, "oocyte" refers to a female germ cell. The oocyte analyzed according to the methods of the invention is obtained prior to fertilization, and the analysis is performed in vitro.

"Pre-implantation embryo" or "embryo" is used herein to refer typically to an in vitro fertilized oocyte with two pronuclei (up to and including a blastocyst) but which has not implanted in the lining of the female reproductive tract. In general, in one embodiment, the pre-implantation embryo contains between about 2 and about 8 cells (i.e., the embryo is assessed between about 18 and about 70 hours post-fertilization), although these ranges may vary among species. Typically, the quality assessment for a human or a mouse embryo is performed on an embryo containing between 2 and 8 cells.

"Cell from an embryo" refers to a single cell biopsied from the embryo. Embryo biopsy is a procedure that involves removing one or more cells from the embryo before it is transferred to the mother's uterus. It is typically performed for testing the embryo for specific genetic disorders. The methods of the present invention can be performed to the cells prior to performing a genetic analysis.

Given the intimate physical and metabolic contact between the cumulus granulosa cells and the oocyte, FLIM-acquired data of these heterologous cells has been shown to correlate with oocyte health. Such an approach circumvents any potential harm of illumination to the oocytes, and also circumvents any need for clinical trials to prove safety. The terms "cumulus cell" and "granulosa cell" as used herein refer to cumulus cells that are specialized granulosa cells surrounding and nourishing the oocyte. These cells surround the fully-grown oocyte to form a cumulus-oocyte complex ("COC"). The terms cumulus oophorus cells, cumulus granulosa cells, cumulus oophorous granulosa cells, granulosa-cumulus cells are used to make a distinction between these cells and the other functionally different subpopulation of granulosa cells at the wall of the Graafian follicle. Cumulus cells provide key products for the acquisition of developmental competence and differ from granulosa cells in their hormonal responses and growth factors they produce. The absence of cumulus cells or insufficient numbers of cumulus cells impairs embryo production. Denuded oocytes in culture cannot undergo normal fertilization with standard insemination. Cumulus cells are required for the successful maturation of oocytes. These cells synthesize an abundant muco-elastic extracellular matrix, which promotes oocyte extrusion from the follicle, a 20-40 fold increase in the volume of the cumulus mass, and probably also functions as a selective barrier for sperm (Salustri, 2000). For cellular and molecular events during oocyte maturation and the formation of the extracellular matrix of the cumulus-oocyte complex see also: Russel and Salustry (2006) and Kimura et al (2007). Cumulus cells show high expression of many enzymes of the glycolytic pathway and also neutral amino acid transporters. Their expression is promoted by paracrine factors secreted by oocytes (Eppig et al, 2005; Sugiura et al, 2005), which themselves are unable to take up L-alanine and poorly metabolize glucose for energy production and thus depend on cumulus cells for their provision (Biggers et al, 1967; Colonna and Mangia, 1983; Donahue and Stern, 1968; Eppig et al, 2005; Haghighat and Van Winkle, 1990; Leese and Barton, 1984, 1985). As the cumulus cells provide the growth environment for the oocyte, their metabolic state can be used as a proxy of the metabolic state of the oocyte they support. Accordingly, in one aspect of all the embodiments of the invention the method uses one or more cumulus cells to select an oocyte for in vitro fertilization or for excluding an oocyte from in vitro fertilization. The cumulus cells are obtained from around an oocyte prior to insemination or ICSI, and the analysis is performed in vitro.

The cells are typically placed in a well suitable for imaging and comprising cell culture medium at 37° C.

The "reference value" as referred to herein, is typically assessed using normal healthy cells of comparable origin, such as normal healthy oocytes, normal healthy embryos, cumulus cells around a normal healthy oocyte or cells from a normal healthy embryo. The reference values are typically a range from averaged experiments, and are typically pre-determined although assays including a healthy reference cell of similar origin are also provided.

The methods of the invention use a device that is typically a self-contained, microscope setting, such as a box, such as a table-top microscope box that is typically used at in vitro fertilization clinics to select oocytes for fertilization and embryos for transfer.

The methods are based on use of fluorescence lifetime imaging microscopy (FLIM) of metabolic state of the oocytes or embryos. The interior of the device comprises, or consists essentially of the microscope and all the peripherals, as well as an environmental chamber enclosing the microscope stage. A small slot in the microscope exterior allows custom, multi-well plates containing granulosa cells, oocytes or embryos or cells biopsied from an embryo to be inserted onto the microscope stage. A screen monitor, such as a touch-screen monitor, for example located on the device's exterior, contains controls and displays acquired data.

The device can be used on oocytes and embryos as well as cumulus cells and cells isolated from an embryo that can be acquired by any procedure and placed in any media. Thus the methods are easily compatible with the current practices in in vitro fertilization clinics and other settings where assessment of embryos or oocytes is performed.

Living cells possess an intricately regulated system of energy-producing and energy-utilizing chemical reactions. Metabolic reactions that are involved in energy generation break down macromolecules such as carbohydrate, lipid, or protein. Most of the energy-generating metabolic pathways of the cell eventually result in the production of acetyl coenzyme A (acetyl CoA). For example, carbohydrates are metabolized to pyruvate, which is oxidized to acetyl CoA by the pyruvate dehydrogenase system.

Acetyl CoA is completely oxidized in a cyclic series of oxidative reactions alternately referred to as the tricarboxylic acid (TCA) cycle, the Krebs cycle or the citric acid cycle. Although certain of the TCA cycle enzymes are also found in the cytosol, where the enzymes function in other metabolic pathways, all of the TCA cycle enzymes are located in the mitochondria. The oxidation of acetyl CoA in one complete TCA cycle results in the production of two $CO_2$ molecules, one high energy phosphate bond (such as that present in GTP) and four reducing equivalents, i.e., three NADH and one $FADH_2$ from three NAD+ and one FAD, respectively.

Measurement of NADH and FAD has been previously used in cell cultures and analyses of precancerous epithelia (Skala et al., PNAS 104(49): 19494-19499, 2007). Skala et al. showed that a decrease in protein-bound NADH, and an increase in protein bound FAD fluorescence lifetime was associated with different states of epithelial cancer. It has also been shown that the fluorescent lifetime of free and protein-bound NADH decrease with hypoxia (Bird et al. Cancer Res. 65: 8766-8773, 2005; Schneckenburger et al., J. Fluorescence 14: 649-654, 2004) and decrease in pre-cancers of hamster cheek pouch model of oral cancer in vivo (Skala et al. J. Biomed. Opt. 12:024014, 2007).

It has been suggested that measuring pyruvate levels in oocyte/embryo culture media as a means of assessing metabolic activity is inadequate for a number of reasons. For example, the contribution of pyruvate to the media from cumulus cells surrounding the oocyte cannot be predicted. In addition, the metabolic profile of the oocyte/embryo is complicated by the changing nutrient (e.g., substrate) requirements of the developing embryo from immature oocyte to blastocyst. In the oocyte and early stage embryo, the vast majority of pyruvate that is taken up by the cell is channeled via acetyl CoA into the mitochondrial TCA cycle and oxidative phosphorylation (Wales, R. et al, (1970) Aust. J. Biol. Sci. 23, 877-887). Pyruvate is required to support the first and second cleavage divisions of the embryo in culture (Biggers, J. et al, (1967) Proc. Natl. Acad. Sci. U.S.A. 58(2), 560-567), whereas glucose is unable to support development until the four-cell stage. Glucose is the predominant nutrient required by the blastocyst (Brinster, R. et al, (1966) Exp. Cell Res. 42, 303-315). Cells in culture exhibit different nutrient requirements over time. For example, the oxidative metabolism of cultured cells declines over time; such cells become increasingly dependent on anaerobic glycolysis with concomitant lactate production (Morgan, M. et al, (1981) Biosci. Rep. 1, 669-686). Thus, for example, mouse blastocysts which have been cultured in vitro produce almost twice as much lactate as blastocysts which are freshly collected (Gardner, D. et al, (1990) J. Reprod. Fertil. 88, 361-368). Therefore, the simple measurement of pyruvate (nutrient) in culture media is not necessarily a reliable or accurate measure of the mitochondrial or metabolic status of the oocyte/embryo.

The oocyte/embryo contains a steady-state concentration of NADH that is present in the cell(s) as a result of metabolic reactions taking place in the mitochondria (e.g., tricarboxylic acid cycle and electron transport) and in the cytosol (e.g., glycolysis). Although one might expect to find a correlation between metabolic activity and oocyte/embryo viability, past efforts failed to establish any such direct correlation. For example, a study by Conaghan et al, J. Assist. Reprod. Genet 10(1): 21-30, 1993, reported that pyruvate uptake by human embryos was not predictive of those that successfully implanted.

The findings in U.S. Pat. No. 5,541,081 suggested that to obtain information about the metabolic state of an embryo/oocytes using NADH, one must first reduce the endogenous NADH concentration of the oocyte/embryo by placing it in a control medium and obtaining at least one control NADH fluorescence measurement. After the control measurement, the oocyte/embryo was then subjected to a different medium with a nutrient for a time period and the change in the NADH concentration was observed. This analysis is not only time consuming but also subjects the embryo/oocyte to an additional and unnecessary stress when it is moved from special medium to another.

Contrary to the prior reported methods for embryo assessment, the method of the present invention allows direct analysis of NADH and/or FAD inside an embryo/oocyte/cumulus cell/cell from embryo without subjecting the embryo/oocyte/cumulus cell/cell from embryo to changes in its culture medium. Due to the specificity of FLIM, we have shown that we can observe the fluorescent lifetime of protein bound and free NADH and/or FAD which we have found is indicative of the metabolic activity of the embryo/oocyte and predictive of, e.g., implantation success.

Fluorescence-lifetime imaging microscopy (FLIM) is an imaging technique for producing an image based on the differences in the exponential decay rate of the fluorescence from a fluorescent sample. FLIM can be used as an imaging technique in confocal microscopy, two-photon excitation microscopy, and multiphoton tomography.

The lifetime of the fluorophore signal, rather than its intensity, is used to create the image in FLIM. This has the advantage of minimizing the effect of photon scattering in thick layers of sample.

A fluorophore which is excited by a photon will drop to the ground state with a certain probability based on the decay rates through a number of different (radiative and/or nonradiative) decay pathways. To observe fluorescence, one of these pathways must be by spontaneous emission of a photon. This can be utilized for making non-intensity based measurements in chemical sensing.

Fluorescence lifetimes can be determined in the time domain by using a pulsed source.

Time-correlated single-photon counting (TCSPC) is usually employed. More specifically, TCSPC records times at which individual photons are detected by something like a photo-multiplier tube (PMT) or an avalanche photo diode (APD) after a single pulse. The recordings are repeated for additional pulses, and after enough recorded events one is able to build a histogram of the number of events across all of these recorded time points. This histogram can then be fit to a function that contains parameters of interest, and thus the parameters can accordingly be extracted. 16~64 multi-channel PMT systems have been commercially available, whereas the recently demonstrated CMOS single-photon avalanche diode (SPAD)-TCSPC FLIM systems can offer additional low-cost options.

Pulse excitation is still used in the gating method. Before the pulse reaches the sample, some of the light is reflected by a dichroic mirror and gets detected by a photodiode that activates a delay generator controlling a gated optical intensifier (GOI) that sits in front of your CCD detector. The GOI only allows for detection for the fraction of time when it is open after the delay. Thus, with an adjustable delay generator, one is able to collect fluorescence emission after multiple delay times encompassing the time range of the fluorescence decay of the sample.

Alternatively, fluorescence lifetimes can be determined in the frequency domain by a phase-modulated method. The intensity of a continuous wave source is modulated at high frequency, by an acousto-optic modulator for example, which will modulate the fluorescence. Since the excited state has a lifetime, the fluorescence will be delayed with respect to the excitation signal, and the lifetime can be determined from the phase shift. Also, y-components to the excitation and fluorescence sine waves will be modulated, and lifetime can be determined from the modulation ratio of these y-components. Hence, 2 values for the lifetime can be determined from the phase-modulation method. Consequently, if the lifetimes that are extracted from the y-component and the phase do not match, it means that you have more than one lifetime species in your sample.

FLIM has primarily been used in biology as a method to detect photosensitizers in cells and tumors as well as FRET in instances where ratiometric imaging is difficult. The technique was developed in the late 1980s and early 1990s (Bugiel et al. 1989. König 1989) before being more widely applied in the late 1990s (Oida T, Sako Y, Kusumi A (March 1993). "Fluorescence lifetime imaging microscopy (flimscopy). Methodology development and application to studies of endosome fusion in single cells". Biophys. J. 64 (3): 676-85). In cell culture, it has been used to study EGF receptor signaling (Wouters F S, Bastiaens P I (October 1999). "Fluorescence lifetime imaging of receptor tyrosine kinase activity in cells". Curr. Biol. 9 (19): 1127-30) and ErbB1 receptor trafficking (Verveer P J, Wouters F S, Reynolds A R, Bastiaens P I (November 2000). "Quantitative imaging of lateral ErbB1 receptor signal propagation in the plasma membrane". Science 290 (5496): 1567-70). FLIM imaging is particularly useful in neurons, where light scattering by brain tissue is problematic for ratiometric imaging (Yasuda R (October 2006). "Imaging spatiotemporal dynamics of neuronal signaling using fluorescence resonance energy transfer and fluorescence lifetime imaging microscopy". Curr. Opin. Neurobiol. 16 (5): 551-61). In neurons, FLIM imaging using pulsed illumination has been used to study Ras (Harvey C D, Yasuda R, Zhong H, Svoboda K (July 2008). "The spread of ras activity triggered by activation of a single dendritic spine". Science 321 (5885): 136-40), CaMKII, Rac, and Ran (The design of Forester (fluorescence) resonance energy transfer (FRET)-based molecular sensors for Ran GTPase, in press P. Kalab, J. Soderholm, Methods (2010) family proteins). FLIM has also been used in clinical multiphoton tomography to detect intradermal cancer cells as well as pharmaceutical and cosmetical compounds.

The cells in the present method can be analyzed in any suitable cell culture medium used for embryo/oocyte/cumulus cell/cell from embryo. Thus, the present methods avoid subjecting the cells to any extraordinary medium changes. Moreover, because there is no need to change the metabolic state of the cell, like e.g., in the '081 patent, no additional time is needed for the analysis, making the analysis fast and convenient.

The measurement consists of acquiring a single FLIM image per cell, which can be obtained rapidly and non-invasively or minimally invasively. Typically, it takes about 1-5 minutes, sometimes 30 seconds to 2 minutes to load a sample containing the cells to be studied and only seconds to acquire the data after which the oocyte/embryo that has been analyzed can either be selected for further fertilization or implantation or discarded as not optimally fit for these procedures.

The FLIM measurement is taken directly inside the embryo using the autofluorescence of nicotinamide adenine dinucleotide (NADH) or flavin adenine dinucleotide (FAD) both molecules involved in cellular metabolism.

In the methods of the present invention, the acquired data are typically subsequently averaged over the entire cell, because subcellular information is unnecessary, producing one FLIM curve per cell.

While we have used mouse embryos and oocytes in our examples provided herein, the assay will not need to be altered when analyzing human cells. The metabolic state of human and mouse embryos and oocytes are comparable during these stages of development and thus the results obtained with mouse oocytes/embryos can be directly applied to human cells as well.

In essence, the method of the invention comprises exposing a test cell to a fluorescence lifetime imaging microscope (FLIM) to acquire a fluorescence lifetime histogram of auto-fluorescence of endogenous NADH and/or FAD for the test cell. The test cell can be an oocyte or an oocyte-associated cumulus cell or an embryo or a cell from the embryo.

Before the exposure, the test cell can be in or be placed in any normal cell culture medium used in maintaining the embryos/oocytes at the clinic. Culture media for embryo development should meet the metabolic needs of pre-implantation embryos by addressing amino acid and energy requirements based on the specific developmental stage of the embryo.

Various culture media are and have been used in ART methods and any of them can be used in the methods of the invention. The following provides some examples of culture media. Culture media, like Earle, Ham's F10, Tyrode's T6 and Whitten's WM1 were based on different salts and were constructed to support the development of somatic cells and cell lines in culture. These culture media, known as physiological salt solutions, were used by Robert Edwards for his first successful In Vitro Fertilization (IVF). These media were formulated for use with or without serum supplementation, depending on the cell type being cultured. The Ham's Nutrient Mixtures were originally developed to support growth of several clones of Chinese hamster ovary (CHO) cells, as well as clones of HeLa and mouse L-cells.

Menezo et al., 1984, suggested adding serum albumin as a source for amino acids. The serum protein ensures that oocytes and embryos do not adhere to the glass surface of the pipette used to manipulate them. The medium entitled B2, is still in use today. In 1985 Quinn et al. published in the journal Fertility and Sterility a formula entitled Human Tubal Fluid (HTF), which mimics the in vivo environment to which the embryo is exposed. The formulation of HTF was based on the known chemical composition of the fluids in human fallopian tubes as known at that time. This medium is based on a simple balanced salt solution without amino acids; however, the concentration of potassium was adjusted to that measured in the human female reproductive tract. This medium was found to be better compared with earlier media developed.

The supplementation of the HTF medium with either whole serum or with serum albumin became a gold standard for the production of culture medium for human embryos transferred on day 2 or day 3 of culture, for example 1-4 days in culture, 2-3 days in culture, 2-4 days in culture.

It is typically considered that culturing embryos involves addressing specific needs depending on the developmental stage of the embryo. Energy source requirements evolve from a pyruvate-lactate preference while the embryos, up to the 8-cell stage, are under maternal genetic control, to a glucose-based metabolism after activation of the embryonic genome that supports their development from 8-cells to blastocysts. This observation lead to the development of the first commercial media. The culture media developed was based on HTF: both media were free of inorganic phosphate, glucose and amino acids. Pool and his colleagues formulated HTF which was free of glucose and phosphate. Cleaving embryos use pyruvate and lactate as energy sources and non-essential amino acids (NEAA) for protein metabolism. From the 8-cell stage the major energy source is glucose and for protein metabolism the embryos use essential amino acids (EAA). These findings lead to development of composition of two culture media G1 and G2 that are to be used in sequence. G1 supports the in-vitro development of the fertilized oocyte, the zygote, to the 8-cell stage, and G2 from 8-cells to blastocyst. Several modifications to these media also exist and are well known to one skilled in the art. Sequential media are now being used successfully in IVF treatment all over the world.

Any of the above-discussed media may be used when imaging the test cells according to the methods of the invention.

The typical composition of the embryo culture medium includes: culture media containing a phosphate buffer or Hepes organic buffer are used for procedures that involve handling of gametes outside of the incubator, flushing of follicles and micromanipulation. The pH and osmolality for most culture media utilize a bicarbonate/$CO_2$ buffer system to keep pH in the range of 7.2-7.4. The osmolarity of the culture medium should be in the range of 275-290 mosmol/kg. Similar conditions should optimally be maintained while imaging the cells according to the methods of the invention.

In addition, the human oocyte is temperature-sensitive and a humidified incubator with a temperature setting of 37.0-37.5° C. should be used for oocyte fertilization and embryo culture. Similar temperature should optimally be maintained while imaging the cells according to the methods of the invention.

Embryos should be cultured under paraffin oil, which prevents evaporation of the medium preserving a constant osmolarity. The oil also minimizes fluctuations of pH and temperature when embryos are taken out of the incubator for microscopic assessment. Paraffin oil can be toxic to gametes and embryos; therefore, batches of oil must be screened and tested on mouse embryos before use in culture of human embryos. The oil does not need to be removed to perform the FLIM analysis of the invention.

The medium is also composed of 99% water. Purity of the water is important, and is typically achieved by ultrafiltration.

Albumin or synthetic serum is typically added in concentrations of 5 to 20% (w/v or v/v, respectively). The commercial media typically includes synthetic serum in which the composition is well known.

Commercial IVF media typically comprises, for example, one or more of the following components: synthetic serum, recombinant albumin, salt solution in MTF, NaCl, KCl, $KH_2PO_4$, $CaCl_2 2H_2O$, $MgSO_4 7H2O$, $NaHCO_3$, and carbohydrates.

Carbohydrates are present in the female reproductive tract. Their concentrations vary throughout the length of the oviduct and in the uterus, and are also dependent on the time of the cycle.

Together with the amino acids carbohydrates are the main energy source for the embryo. Culture media that support the development of zygotes up to 8-cells contain pyruvate and lactate. Some commercial media are glucose free, while others add a very low concentration of glucose to supply the needs of the sperm during conventional insemination.

Media that support the development of 8-cell embryos up to the blastocyst stage contain pyruvate and lactate in low concentrations and a higher concentration of glucose.

Amino acids supplement of the culture medium with amino acids is necessary for embryo development. Media that support the development of zygotes up to 8-cells are often further supplemented with non-essential amino acids. Proline, serine, alanine, asparagine, aspartate, glycine, glutamate. Media that support the development of 8-cell embryos up to the blastocyst stage are typically supplemented with essential amino acids: Cystine, histidine, isoleucine, leucine, lysine, methionine, valine, arginine, glutamine, phenylalanine, threonine, tryptophane.

The majority of ART laboratories use culture media containing antibiotics to minimize the risks of microbial growth. The most commonly used antibiotics being Penicillin (β-lactam Gram-positive bacteria disturbs cell wall integrity) and Streptomycin (Aminoglycoside Gram-negative bacteria disturbs protein synthesis). The anti-bacterial effect of penicillin is attributed to its ability to inhibit the synthesis of peptidoglycan, unique glycoproteins of the bacterial cell wall. Streptomycin and gentamycin belong to the aminoglycoside group of antibiotics which exert their antibacterial effect by inhibiting bacterial protein synthesis. The use of genthamicine is still controversial and it is not being used by every laboratory.

Often, the culture medium also comprises EDTA which is used as a chelator in medium that supports the embryo from the zygote stage to 8-cells and prevents abnormal glycolysis.

As noted before, the methods of the invention are not dependent on the type of the medium. The cells should remain in the medium and conditions they are cultured to avoid additional stress to them during the FLIM analysis.

The method further comprises averaging the fluorescence lifetime histogram of NADH auto-fluorescence or FAD auto-fluorescence or both over the entire test cell, or the cytoplasm of the test cell, or mitochondria of the test cell.

To be able to select the healthy cells for further assisted reproductive methods, the method also comprises comparing the averaged fluorescence lifetime histogram from the test cell to an averaged fluorescence lifetime histogram reference value to determine if the measured averaged fluorescence lifetime histogram from the test cell differs statistically from that of the reference value. The comparing is typically made using a non-human machine typically using a computer executable software which includes a comparison between a reference value and the value from each individual cell FLIM analyses.

Similarly to NADH, also autofluorescence of FAD can be analyzed using FLIM in the methods of the present invention.

The FLIM curves of NADH crom cells exhibit a double exponential decay with a long lifetime (about 2.5 nanoseconds (ns)) corresponding to protein bound NADH and a short lifetime (about 0.4 ns) corresponding to free NADH. Thus, the FLIM curve is a double exponential with the relative fraction of the long and short lifetimes reflecting the relative fraction of protein bound and free NADH. This provides a direct readout of the metabolic state of the cell (Lacowciz et al., 1992). The long lifetime might vary from 1-3 (nanoseconds) ns and the short life time might vary from 0.2-0.7 ns.

The precise value of these lifetimes in the free and bound states depends on a variety of cellular factors, such as pH (Ogikubo et al., 2011). The relative fraction of the long and short lifetimes, and the precise value of these lifetimes are typically determined by using a least-squares fit. However, Bayesian inferences approaches, may allow even more precise parameter estimates and reference estimates with fewer number of photons, allowing even less light to be used to obtain further reliability and further minimizing sample exposure.

The absorption and fluorescence spectra of NADH (the reduced form) have been well characterized at different levels of organization, i.e., in solution, mitochondria and cell suspensions, tissue slices, and organs in vitro and in vivo. NADH has an optical absorption band at about 300 to 380 nm and a fluorescence emission band at 420 to 480 nm. The spectra are considered the same, although there are small differences in the shape and maxima of the spectra for different environments and measurement conditions. However, there is a universal agreement that the intensity of the fluorescence band, independent of the organization level of the environment, is proportional to the concentration of mitochondrial NADH (the reduced form), particularly when measured in vivo from a tissue (see, e.g., review by Avraham Mayevsky and Gennady G. Rogatsky, Am J Physiol Cell Physiol February 2007 vol. 292 no. 2 C615-C640).

Accordingly, in some aspects of all the embodiments of the invention, the direct autofluorescence of NADH can be analyzed with FLIM using a wavelength of about 740 nm in two-photon fluorescence excitation and using an emission bandpass filtered centered around about 460 nm.

In some aspects of all the embodiments of the invention, the direct autofluorescence of NADH can also be analyzed with FLIM using a wavelength of about 340 nm in one-photon fluorescence excitation and using an emission bandpass filtered centered around about 460 nm.

In some aspects of all the embodiments of the invention, the direct autofluosescence of FAD can be analyzed with FLIM using a wavelength of about 900 nm in two-photon fluorescence excitation and using an emission bandpass filtered centered around about 550 nm.

The direct autofluorescence of FAD can be analyzed with FLIM using a wavelength of about 450 nm in one-photon fluorescence excitation and using an emission bandpass filtered centered around about 550 nm.

The embryo analyzed according to the methods of the invention is a pre-implantation embryo, and the analysis is performed in vitro. Similarly, a cell obtained from an embryo is obtained from a pre-implantation embryo and the cell biopsy is performed in vitro.

One can combine the analysis using FLIM of NADH and FAD by simply exposing the cells sequentially to wavelength suitable for NADH and then to FAD or wavelength suitable for imaging the fluorescence lifetime of FAD and then NADH. Accordingly, in some aspects of all the embodiments of the invention the method comprises a sequential analysis of FAD and NADH.

The analysis typically only takes a short time, such as 30 seconds to 5 minutes and can be multiplexed and automated.

Thus, we provide a method for assessing the quality of an oocyte or an embryo, the method comprising (a) exposing, in a medium, granulosa cell(s), oocyte, the embryo or cell(s) from the embryo to a fluorescence lifetime imaging microscopy (FLIM) to acquire a fluorescence lifetime histogram of auto-fluorescence of NADH in the granulosa cells, oocyte, the embryo or cell(s) from the embryo; (b) averaging the fluorescence lifetime histogram of auto-fluorescence of NADH over the entire granulosa cell, oocyte, the embryo or cell(s) from the embryo; (c) fitting the averaged fluorescence lifetime histogram of auto-fluorescence of NADH to a sum of two exponentials; and (d) selecting for in vitro fertilization or implantation the oocyte or embryo when one detects a cell, whether granulosa cells, oocyte, the embryo or cell(s) from the embryo, in which the alpha is less than an alpha reference value and the beta is less than a beta reference value or discarding the oocyte or embryo from in vitro fertilization when one detects a cell, whether granulosa cells, oocyte, the embryo or cell(s) from the embryo, in which the alpha is equal or more than the alpha reference value and if the beta is equal or more than the beta reference value. The cell can be an embryo, oocyte, or a cell extracted from en embryo or a cumulus cell surrounding an oocyte. In some aspects, the method further comprises a step of in vitro fertilizing the oocyte when one detects a cell, either oocyte or one or more cumulus cell from around the oocyte with the alpha is less than an alpha reference value and the beta is less than a beta reference value, or implanting the embryo when one detects a cell from the embryo or an embryo with the alpha is less than an alpha reference value and the beta is less than a beta reference value.

In some aspects of all the embodiments of the invention, the alpha reference value is between 1 and 4, such as 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, or 2-3, or 2-4, or 1-2, or 1-3. In some aspects of all the embodiments of the invention, the alpha reference value is 1.7.

In some aspects of all the embodiments of the invention, the beta reference value is 2000 ps-3000 ps, or 2000-2500, or 2500-3000, or 2000-2250, or 2000-2750. In some aspects of all the embodiments the beta reference value is 2250 ps (picoseconds). FIG. 1 provides an example of suitable alpha and beta values for evaluation of oocytes.

While our preliminary analyses have been performed using mouse oocytes as a model. The metabolic state of oocytes and embryos in both humans and mice is practically identical. Therefore, the reference values obtained from the metabolic state FLIM analysis in a mouse cumulus cell, oocyte and/or embryo, can be directly applied to human oocyte and embryo analysis. The reference values can also be obtained from human cumulus cell, oocyte and/or embryo.

In some aspects of all the embodiments of the invention, the FLIM of NADH is performed using a wavelength of about 740 nm in two-photon excitation and using an emission bandpass filter centered around about 460 nm.

In some aspects of all the embodiments of the invention, one obtains FLIM images at different times instead of only acquiring a single image. This kind of time-lapse data would be richer, and thus can provide more information about the cells. However, it will require cells to be in the device for longer periods of time and they would be exposed to more light, thereby slightly increasing the invasiveness of the method.

The described method is typically performed using a system that contains nearly all of the components of a traditional microscope. Thus the method can be combined with analysis of morphological time-lapse data as well.

There are three possible options for performing the FLIM measurements, all of which can be used in the methods of the present invention: two-photon excitation with a point detector, one-photon excitation with a point detector, or one-photon detection with an area detector (i.e. a camera). The table below indicates the advantages of each of the options. We used the two-photon method in our examples.

|  | Two-Photon Point Detector | One-Photon Point Detector | One-Photon Camera |
| --- | --- | --- | --- |
| Sensitivity | Highest | Medium | Lowest |
| Cost | Highest | Medium | Lowest |
| Robustness | Lowest Robustness | Medium Robustness | Most Robust |
| Complexity | Simple Optical Setup with Stage Scanning Imaging | Complex Optical Setup with Stage Scanning Imaging | Simple Optical Setup |
| Safety Considerations | Long Wavelength (reduces possible damage) | Shorter Wavelength | Shorter Wavelength |

EXAMPLES

We obtained preliminary data on FLIM of NADH in mouse oocytes. The preliminary data was acquired on a FLIM system. The microscope consists of a ti-sapphire femtosecond laser (Spectra-Physics), an inverted microscope base (Nikon), a scan head (Becker & Hickl), a hybrid PMT detector (Hamamatsu), and electronics for time correlated single photon counting (Becker & Hickl). This microscope was assembled to acquire the preliminary data.

Oocytes were placed in a medium on the microscope stage and imaged. A single image of each oocyte was analyzed by averaging the FLIM data over the entire oocyte. The acquired fluorescence lifetime histogram from NADH, averaged over the entire oocyte, was fit to a sum of two exponentials. The parameter alpha, is the ratio of the amplitude of the two exponentials, the parameter, beta, is the lifetime of the longer exponential (in picoseconds).

Unperturbed oocytes exhibit a range of values of alpha and beta (FIG. 1, circles). As seen in FIG. 1, oocyte quality depends on oocyte metabolic state. Oocyte metabolic state can be rapidly, non-invasively, and quantitatively measured by Fluorescence Lifetime Imaging Microscopy (FLIM) of FAD or NADH. Two parameters (alpha and beta) are extracted from FLIM measurements of NADH (or FAD) in oocytes. In the example, we used mouse oocytes but similar calculations are expected to work for human oocytes, as the mammalian cells, such as mouse and human cells are relatively similar, particularly relating to their metabolic state, at this stage. Each point corresponds to data from a single oocyte. Perturbing oocytes by specific metabolic inhibitors (black crosses), or non-specific damage (triangles) causes both parameters to increase. Unperturbed oocytes (circles) exhibit a range of values of alpha and beta. These parameters are indicative of oocyte quality.

Alpha and beta both increase when oocytes are perturbed by either applying a metabolic inhibitor (FIG. 1, black crosses) or greatly increasing laser power to intentionally damage the oocytes (FIG. 1, triangles). Such damage does not occur at the low laser powers used for imaging.

Our results show that low values of alpha and beta are indicative of oocyte and embryo health. All perturbed oocytes are found in the upper quadrant with alpha greater than 1.7 and beta greater than 2250. This shows that these values of alpha and beta can be used as cutoffs with oocytes above these values rejected as likely being unhealthy, and oocytes below these values deemed healthy and selected for use.

The metabolism of human and mouse oocytes are very similar, and thus, cutoff values of alpha and beta established for mice can be used for human analyses as well.

The values of alpha and beta are obtained quantitatively, rapidly, and objectively. Thus the described approach is highly useful in in vitro fertilization clinics.

REFERENCES

The references cited herein and throughout the specification are herein incorporated by reference in their entirety.

Botros, L., Sakkas, D. and Seli, E. Metabolomics and its application for non-invasive embryo assessment in IVF. Molecular Human Reproduction Vol. 14, No. 12 pp. 679-690, 2008.

Lakowciz, J. R., Szmacinski, H., Nowaczyk, K., and Johnson, M. L. Fluorescence lifetime imaging of free and protein-bound NADH. PNAS. 1992. 89. 1271-1275

Ogikubo, S., et al, Intracellular pH Sensing Using Autofluorescence Lifetime Microscopy. Journal of Physical Chemistry B. 2011. 115, 10385-10390.

Scott R T, Kerry F, Su J, Tao X, Scott K, Treff N. Comprehensive chromosome screening is highly predictive of the reproductive potential of human embryos: a prospective, blinded, non-selection study. Fertil Steril 2012; 97:870-5.

Vergouw C G, Kieslinger D C, Kostelijk E H, Botros L L, Schats R, Hompes P G, Sakkas D, Lambalk C B. Day 3 embryo selection by metabolomic profiling of culture medium with near-infrared spectroscopy as an adjunct to morphology: a randomized controlled trial. Hum Reprod. 2012; 27(8):2304-11.

Seli, E. and Brommer, J. G. Assessment of embryo viability in assisted reproductive technology: shortcomings of current approaches and the emerging role of metabolomics. Current Opinion in Obstetrics and Gynecology. 2008, 20:234-241

Society for Assisted Reproductive Technology (SART). Assisted reproductive technology success rates. National summary and fertility clinic reports. Atlanta, Ga.: Centers for Disease Control and Prevention; 2005

Stringaria, C., Cinquinb, A., Cinquinb, O., Digmana, M. A., Donovan, P. J., and Grattona, E. Phasor approach to fluorescence lifetime microscopy distinguishes different metabolic states of germ cells in alive tissue. PNAS. 2011. 108: 33. 13582-13587

Uyar A, Seli E. Embryo assessment strategies and their validation for clinical use: a critical analysis of methodology. Curr Opin Obstet Gynecol. 2012 June; 24(3):141-50

Zipfel W R, et al. (2003) Live tissue intrinsic emission microscopy using multiphotonexcited native fluorescence and second harmonic generation. Proc Natl Acad Sci USA 100:7075-7080. Botros, L., Sakkas, D. and Seli, E. Metabolomics and its application for non-invasive embryo assessment in IVF. Molecular Human Reproduction Vol. 14, No. 12 pp. 679-690, 2008

Lakowciz, J. R., Szmacinski, H., Nowaczyk, K., and Johnson, M. L. Fluorescence lifetime imaging of free and protein-bound NADH. PNAS. 1992. 89. 1271-1275

Ogikubo, S., et al., Intracellular pH Sensing Using Autofluorescence Lifetime Microscopy. Journal of Physical Chemistry B. 2011. 115, 10385-10390.

Scott R T, Kerry F, Su J, Tao X, Scott K, Treff N. Comprehensive chromosome screening is highly predictive of the reproductive potential of human embryos: a prospective, blinded, non-selection study. Fertil Steril 2012; 97:870-5.

Vergouw C G, Kieslinger D C, Kostelijk E H, Botros L L, Schats R, Hompes P G, Sakkas D, Lambalk C B. Day 3 embryo selection by metabolomic profiling of culture medium with near-infrared spectroscopy as an adjunct to morphology: a randomized controlled trial. Hum Reprod. 2012; 27(8):2304-11.

Seli, E. and Brommer, J. G. Assessment of embryo viability in assisted reproductive technology: shortcomings of current approaches and the emerging role of metabolomics. Current Opinion in Obstetrics and Gynecology. 2008, 20:234-241

Society for Assisted Reproductive Technology (SART). Assisted reproductive technology success rates. National summary and fertility clinic reports. Atlanta, Ga.: Centers for Disease Control and Prevention; 2005

Stringaria, C., Cinquinb, A., Cinquinb, O., Digmana, M. A., Donovan, P. J., and Grattona, E. Phasor approach to fluorescence lifetime microscopy distinguishes different metabolic states of germ cells in alive tissue. PNAS. 2011. 108: 33. 13582-13587

Uyar A, Seli E. Embryo assessment strategies and their validation for clinical use: a critical analysis of methodology. Curr Opin Obstet Gynecol. 2012 June; 24(3):141-50

Zipfel W R, et al. (2003) Live tissue intrinsic emission microscopy using multiphotonexcited native fluorescence and second harmonic generation. Proc Natl Acad Sci USA 100:7075-7080.

What is claimed herein is:

1. A fluorescence lifetime imaging microscopy system comprising:
   a) an environmental chamber comprising a oocyte in a medium which does not metabolically perturb the oocyte;
   b) a source of fluorescence excitation light which exposes the oocyte to a fluorescence excitation light using
      i. a wavelength of 740 nm in two-photon fluorescence excitation or a wavelength of 340 nm in one-photon fluorescence excitation; and
      ii. a wavelength of 900 nm in two-photon fluorescence excitation or a wavelength of 400 nm in one-photon fluorescence excitation; and configured to provide less fluorescence excitation light than the amount that will perturb the oocyte;

c) a point detector comprising an emission bandpass filter, which sequentially detects the auto-fluorescence emission of endogenous NADH and endogenous FAD of an oocyte exposed to the source of fluorescence excitation light;

d) a computer executable software on a non-human machine which:

builds a fluorescence lifetime histogram of the endogenous NADH and endogenous FAD auto-fluorescence emission;

fits the fluorescence lifetime histogram to a sum of two exponentials to provide a function comprising the parameters:

short lifetime;

long lifetime; and relative fraction of short lifetime vs. long lifetime.

2. The system of claim 1, wherein the oocyte is a candidate for fertilization by assisted reproductive technology.

3. The system of claim 1, wherein the system can detect the metabolic state of the oocyte.

4. The system of claim 1, wherein the system can distinguish the metabolic state of the oocyte as acceptable or abnormal.

5. A method of fluorescence lifetime imaging microscopy, the method comprising:

a) providing a cell or cells in a medium which does not metabolically perturb the cell or cells, wherein the cell or cells comprise at least one cumulus cell obtained from around an oocyte, at least one oocyte, or at least one embryo;

b) illuminating the cell or cells with excitation light;

c) detecting the auto-fluorescence emission of endogenous NADH and/or endogenous FAD of the unperturbed cell or cells using a fluorescence lifetime imaging microscope (FLIM) with an emission bandpass filter set for NADH or FAD auto-fluorescence emission;

d) building a fluorescence lifetime histogram of the NADH and/or FAD auto-fluorescence emission;

e) fitting the fluorescence lifetime histogram of step (d) to a sum of two exponentials to provide a function comprising the parameters:

short lifetime;

long lifetime; and relative fraction of short lifetime vs. long lifetime; and calculating whether the parameters obtained from the fluorescence lifetime histogram from the unperturbed cell or cells differ statistically from parameters obtained from an fluorescence lifetime histogram reference value from a normal healthy cell or cells of the same type;

wherein (i) parameters obtained from the unperturbed cell or cells which do not differ statistically from the reference values indicates that the oocyte from which the at least one cumulus cell was obtained from around, the at least one oocyte, or the at least one embryo is suitable for in vitro fertilization; and (ii) parameters obtained from the unperturbed cell or cells which differ statistically from the reference value indicates that the oocyte from which the at least one cumulus cell was obtained from around, the at least one oocyte, or the at least one embryo is not suitable for in vitro fertilization.

6. The method of claim 5, wherein the excitation light is a wavelength of 740 nm in two-photon fluorescence excitation or a wavelength of 340 nm in one-photon fluorescence excitation; or a wavelength of 900 nm in two-photon fluorescence excitation or a wavelength of 400 nm in one-photon fluorescence excitation.

7. The method of claim 5, wherein the excitation light is less than the amount that will perturb the cell.

8. The method of claim 5, further comprising:

f) fertilizing and/or implanting the oocyte from which the at least one cumulus cell was obtained from around, the at least one oocyte, or the at least one embryo if the parameters obtained from the unperturbed cell or cells do not differ statistically from the reference values, and excluding the oocyte from which the at least one cumulus cell was obtained from around, the at least one oocyte, or the at least one embryo from fertilization and/or implantation if the parameters obtained from the unperturbed cell or cells differ statistically from the reference value.

9. The method of claim 5, comprising sequentially detecting the auto-fluorescence emission of both endogenous NADH and endogenous FAD.

10. The method of claim 5, wherein detecting the auto-fluorescence emission of endogenous NADH or FAD comprises performing the detection in the time domain.

11. The method of claim 5, wherein detecting the auto-fluorescence emission of endogenous NADH or FAD comprises performing the detection in the frequency domain.

12. The method of claim 5, wherein the fluorescence lifetime histogram is averaged over the entire cell or cells, or the cytoplasm of the cell or cells, or the mitochondria of the cell or cells.

13. The method of claim 5, wherein the parameters to be compared between the measurements and the healthy cells are alpha, defined as the ratio of the amplitude of the two exponentials, and beta, defined as the lifetime of the longer exponential.

14. The method of claim 13, wherein the maximum value of alpha from the healthy cells is within the range 1.0-4.0 and the corresponding maximum value of beta of healthy cells is in the range 2000 ps-3000 ps.

15. The method of claim 5, wherein the cell or cells comprise a cumulus cell obtained from around an oocyte.

16. The method of claim 5, wherein the cell or cells comprise an oocyte.

17. The method of claim 5, wherein the cell or cells comprise an embryo.

* * * * *